United States Patent [19]

Nilsson

[11] 3,992,155

[45] Nov. 16, 1976

[54] COLLECTING APPARATUS FOR GASES

[75] Inventor: Bengt Nilsson, Vasteras, Sweden

[73] Assignee: Allmanna Svenska Elektriska Aktiebolaget, Vasteras, Sweden

[22] Filed: Mar. 24, 1976

[21] Appl. No.: 669,803

[30] Foreign Application Priority Data

Feb. 23, 1976 Sweden .............................. 7602085

[52] U.S. Cl. .......................... 23/254 E; 73/421.5 R; 73/422 TC; 137/99

[51] Int. Cl.² .................... G01N 1/26; G01N 27/16; G05D 11/03

[58] Field of Search ............ 23/254 E, 254 R, 255 E, 23/255 R, 232 E, 232 R; 73/23, 25, 26, 27 R, 421.5 R, 422 TC; 137/99

[56] References Cited

UNITED STATES PATENTS

| 3,111,388 | 11/1963 | Horelick et al. .................. 23/232 E |
| 3,530,873 | 9/1970 | Arp et al. ............................... 137/99 |
| 3,672,389 | 6/1972 | McConnell et al. .................. 137/99 |
| 3,680,359 | 8/1972 | Lynch ................................. 73/23 X |
| 3,859,842 | 1/1975 | Bosch ......................... 73/421.5 R X |

Primary Examiner—Robert M. Reese
Attorney, Agent, or Firm—Kenyon & Kenyon Reilly Carr & Chapin

[57] ABSTRACT

A collecting apparatus for gases, particularly when given-off by the oil of an oil-filled transformer in operation, provides for collecting known volumes of the gases and of an oxidizing gas and thereafter mixing these volumes together and causing any hydrocarbon or other burnable gas to burn via the oxidizing gas, to determine the existence and amount of the burnable gas. This permits an evaluation of the transformer oil. The apparatus may be used in other fields.

5 Claims, 5 Drawing Figures

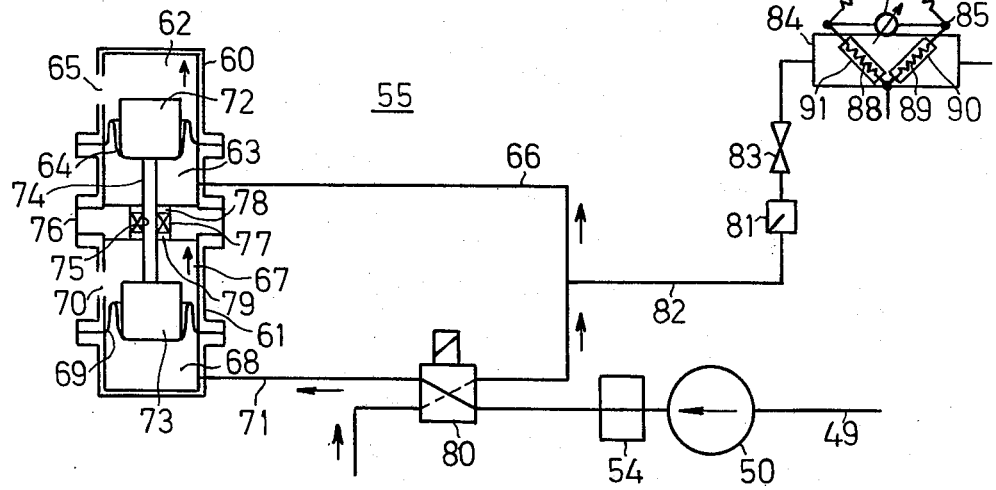
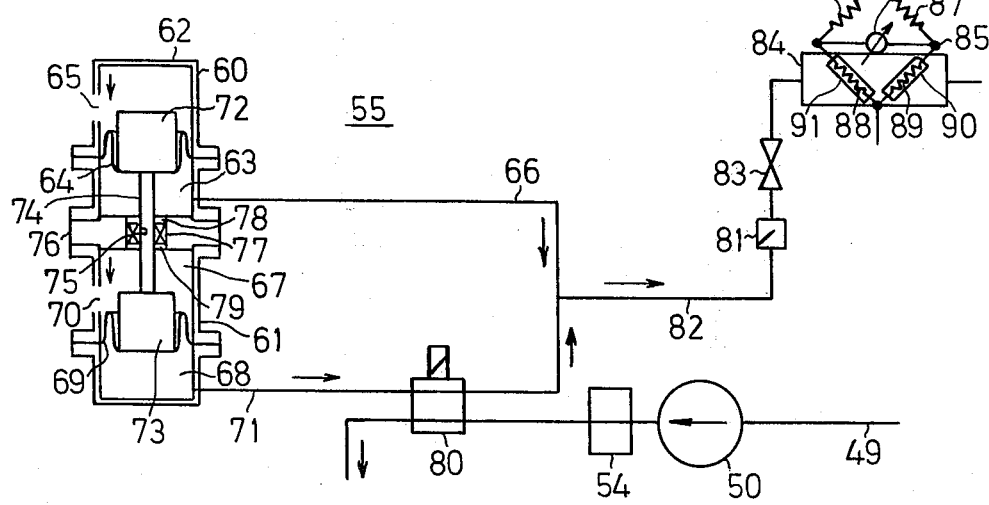

COLLECTING APPARATUS FOR GASES

BACKGROUND OF THE INVENTION

This invention relates to electrical power transformers, particularly of the larger and largest sizes now made and used commercially, which normally use cellulosic electrical insulation, such as pressboard and Kraft paper, in a tank normally filled with transformer oil which impregnates the cellulosic material, the tank being closed or sealed as hermetically as is currently possible, to prevent the entrance of oxygen which has for a long time been considered harmful with respect to the transformer oil. The cellulosic insulation additionally serves to mechanically space electrically conducting parts of differing potentials within the casing, while providing increased electrical insulation strength as compared with an equally thick oil layer. The oil also functions as coolant to carry away heat unavoidably developed by the current-carrying components within the tank.

Such transformers, as currently made by reputable manufacturers, are in operation in many countries and they operate in a successful manner insofar as meeting the requirements currently demanded.

When such a transformer is first put into service, it is filled with transformer oil that is as clean and as free as possible from oxygen or other gases and water, the casing then being sealed as hermetically as is possible today. However, it is known that with time inevitable leakages will cause the oil to increase its oxygen content, and that other gases will accumulate in the tank. Also, the oil will become contaminated with water and solids.

Apparatus is commercially available for filtering and degassing and drying the oil, which can be connected to the transformer, the transformer oil being pumped through this apparatus which then filters the oil and subjects the oil to a high vacuum treatment for degassing and water removal. This apparatus, with a single pass of the oil, is said to be able to reduce the water content in the oil to not more than 5 parts per million (by weight), and the gas content in the oil to less than 0.1% by volume, while removing 99.9% of all particles larger than one micron.

Such an apparatus is used when putting a new transformer in service and possibly when the oil is changed in the transformer.

In spite of that, transformers deteriorate due to different aging processes and aging products.

Many scientific works on aging phenomena in power transformers have been published, and many investigations on the aging of transformers in service have been reported, but insofar as is known, these findings have not been linked together and no practical conclusions have been drawn. The best efforts made so far in the direction of slowing transformer deterioration has been to use the best means available to hermetically seal the transformer tank against the entrance of oxygen and moisture and to use antioxidants in the oil and in the cellulosic material.

During the operation of a sealed or closed transformer having the usual insulation and spacers of cellulosic material, such as pressboard and Kraft paper, and using usual transformer oil insulation, gases are evolved as deterioration products of the insulation materials. The production rate of these gases increases dramatically with increasing temperatures of the materials. This makes it possible to check the state of the transformer insulation by analyzing the gases existing in the transformer.

During development of this invention, it was found that transformer oil, aged at temperatures from 110° C to 170° C in a closed system, virtually ceases to produce hydrocarbon and carbon-oxide gases, when the oil contains less than 2,000 parts per million, by volume, of oxygen. At higher oxygen contents the oil produces substantial volumes of gases, independently of the oxygen content.

In the following, ppm is used to mean parts per million by volume per volume of oil at 0° C and a pressure of 760 mm mercury.

It was further found by aging dry cellulosic transformer insulation in the substantial absence of oxygen, using temperatures up to 180° C for several weeks, that carbon-oxides are produced by pyrolysis, but that substantially no hydrocarbons are produced. Hydrogen can be detected.

Since no hydrocarbons were found in the gases produced by the aging of the cellulosic material, which was Kraft paper, it was concluded that hydrocarbons found during gas analysis of working transformers, probably originated from deterioration of the transformer oil and not from the cellulosic material.

For verification of the above conclusion, experiments were performed where about 200 gm specimens of Kraft paper were heated in the range of 100 to 200° C, with the paper in about 4000 gm of oil containing oxygen. As a result, it was found that the gases produced in the form of hydrocarbons were practically the same as for the transformer oil only, suggesting that the cellulosic insulation of a transformer, at least up to 200° C, does not contribute to the production of hydrocarbons. However, the production rates of carbon-oxides was larger than indicated by the previously described work with the cellulosic material, per se, in a substantially oxygen-free atmosphere, suggesting that the oxygen content of the oil played some part in the production of the carbon-oxides. Inferentially there was the possibility that oxygen contents in the oil even below 2,000 ppm might have some effect on the aging of the cellulosic material when in the presence of the transformer oil, although the oil itself ceases to evolve hydrocarbons.

Therefore, two prolonged heat runs were performed on the same new transformer, this transformer having a rating as follows: 6.3 MVA, 22.5 ± 8.67 percent 11.5 – 6.65 kV, oil weight 5200 kg. This transformer was of a normal construction having coolers and a conservator, and also, of course, was of the sealed or closed type designed to operate under hermetically sealed conditions to the fullest extent possible by the present state of the transformer art.

For a first heat run, the transformer and its coolers were carefully dried and filled with thoroughly degassified oil under vacuum, the conservator being initially completely filled with degassified and substantially oxygen-free oil. The oil in the conservator was then partly replaced by nitrogen. Instead of the usual short tubing between the transformer tank and the conservator, a 10 m long hose with a loop was installed as a replacement for the short tubing, with the intent of minimizing possible transfer of oxygen to the oil in the tank, from the conservator. By closing some of the coolers the transformer was operated at a top oil temperature of 90° C and there held as constant as possible throughout a heat run of 55 hours. Oil samples were taken several times a day for analysis, and it was found that the total gas content of the samples was around 0.3%, the gas being mainly nitrogen and the oxygen content below 300 ppm.

The second heat run was made under the same time and temperature conditions on the same transformer but with the oil containing 30,000 ppm oxygen to determine the effects of oxygen on the production of carbon-oxides and, hydrogen gas found to result from the pyrolysis of the cellulosic material per se, in the substantial absence of oxygen. Even at this 30,000 ppm oxygen content, no hydrocarbon gases were developed, but the development of carbon-oxide gases was increased substantially compared with the first run.

The foregoing led to the discovery that if the oxygen content of the transformer oil was kept below 300 ppm, the rate of the production of the carbon-oxides was radically reduced, whereas operation of the transformer with oil having higher values of oxygen produced a sharp increase in the production rate of these gases.

A change from the transformer oil containing 30,000 ppm of oxygen to one containing less than 300 ppm was found to reduce the production rate of carbon-oxides radically. $CO_2$ is reduced by a factor of at least 5 and CO by a factor of 10. This produces the inevitable conclusion that the life of a transformer of the type described can be increased by a factor of 5 or, and this might possibly be more important, the operating temperature of the transformer can be increased by about 25° C with a life expectancy unchanged over that which would be otherwise considered normal in the case of prior art transformer operation.

The transformer oil in an operating transformer can be kept with an oxygen content under 300 ppm by connection with and operation of the prior art filtering and degassifying apparatus, continuously or substantially continuously during the transformer operation. Therefore, a transformer of the type described preferably should be built to include an integrated filtration and degassification unit.

SUMMARY OF THE INVENTION

In the light of the foregoing, the present invention may be summarized by saying that it comprises a method for operating a transformer of the oil-insulated type, having a tank which is sealed against the entrance of the outer atmosphere to the best extent possible, but to a degree, pervious to the atmosphere, the tank containing the transformer windings insulated by cellulosic material and with the tank filled with transformer oil, the oxygen content of the oil being maintained below 300 ppm continuously while the transformer is in operation. The method is practiced by providing the transformer tank with a degassifying unit of the type operating by subjecting the oil to evacuation, the oil being continuously removed from and returned to the tank through this unit. Preferably, the flow of oil going to this unit is passed through a filter.

It was previously indicated that the ageing of transformer oil produces hydrocarbons, and of the cellulosic insulation, produces carbon-oxides. The degassification unit can provide means for storing any gases or vapors removed from the flowing oil and which are incidental to the removal of any oxygen as required to maintain the critical limit of 300 ppm at least.

The invention further contemplates collection of gases together with the provision of means for determining the relative amounts of combustible and non-combustible gases. If the gas monitor indicates an abnormally high content of gases in the transformer oil the reason, or a contributory reason, may be that the oxygen concentration in the oil has increased so that steps must be taken to eliminate the cause of this increase. If the gases indicated consist mainly of incombustible gases this indicates that there is a leakage of air somewhere. If the indicated gases are instead mainly combustible gases, this indicates that there is a thermal or electrical fault in the transformer.

BRIEF DESCRIPTION OF THE DRAWINGS

A specific example of a transformer embodying the principles of this invention is schematically illustrated by the accompanying drawings, in which:

FIG. 4a diagrammatically shows an apparatus for determining the gas collected via the degassification equipment of FIG. 3; and FIG. 4b is the same as FIG. 4a but shows a different phase in the operation of that apparatus.

DETAILED DESCRIPTION OF THE INVENTION

Figure 1:
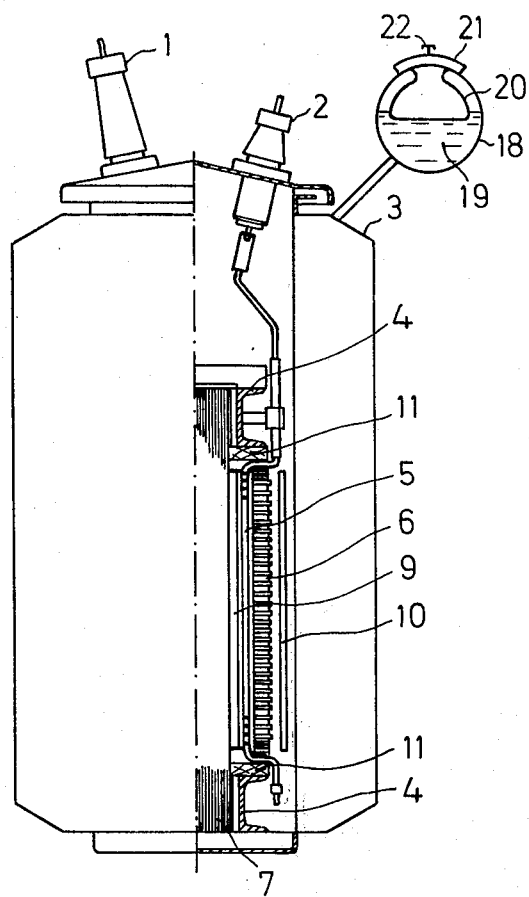
FIG. 1 shows in elevation on the left side and vertical section on the right side, a power transformer of the sealed or closed oil-filled type used to handle the higher voltages and larger amperages currently in use, the sectioned portion revealing enough of the components for an explanation of the principles of this invention.
Figure 2:
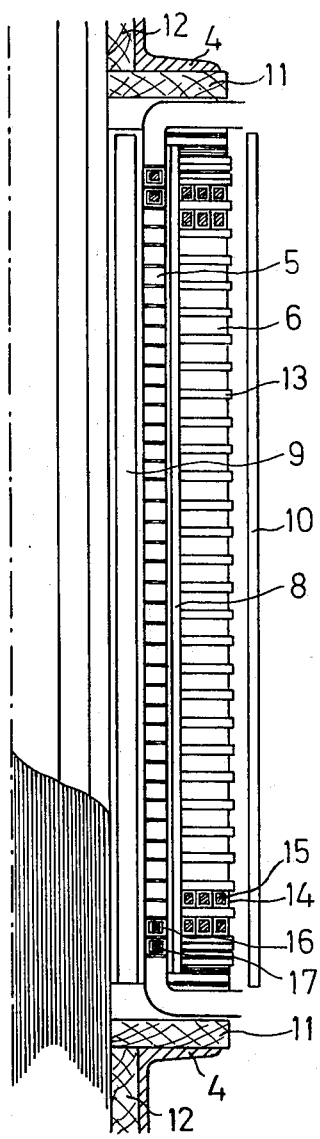
FIG. 2 shows some of the electrical windings and some of the cellulosic insulation on a larger scale than these parts shown in FIG. 1.

In the transformer schematically shown by FIGS. 1 – 2 only parts required to disclose this invention, are represented. 1 designates a high-voltage bushing, 2 a low-voltage bushing, 3 the transformer tank, 4 pressure flanges, 5 the low-voltage winding, 6 the high-voltage winding, 7 the iron core, 8, 9 and 10 insulating cylinders serving as barriers between the low-voltage winding 5 and high-voltage winding 6, and between the low-voltage winding 5 and iron core 7, and between the high-voltage winding 6 and transformer tank 3. 11 designates pressure-loaded spacers in the form of insulating inserts, 12 insulating spacers, 13 pressure-loaded spacer elements, 14 conductor insulation in the high-voltage winding, 15 conductors in the high-voltage winding, 16 conductor insulation in the low-voltage winding, 17 conductors in the low-voltage winding.

Each insulating cylinder 8, 9 and 10 comprises a number of concentric cylinders of cellulosic material, such as pressboard, having a wall thickness of 0.3 – 5 mm. The conductor insulations 14 and 16 comprise a wrapping of several layers of cellulose paper, such as Kraft paper, having a thickness of approximately 50 $\mu$. The pressure-loaded spacer elements 11 and 13 and the insulating spacer 12 consist of pressboard. The transformer tank is completely filled with oil 19, which also partially fills the expansion vessel 18 connected to the transformer by a conduit for the oil. The entire volume of oil is sealed from the atmosphere by a membrane 20 of rubber or metal, which is sealed to the lid 21 of the expansion vessel, the lid being fastened airtightly to the vessel 18. The lid is provided with an escape valve 22 for air above the membrane.

Figure 3:
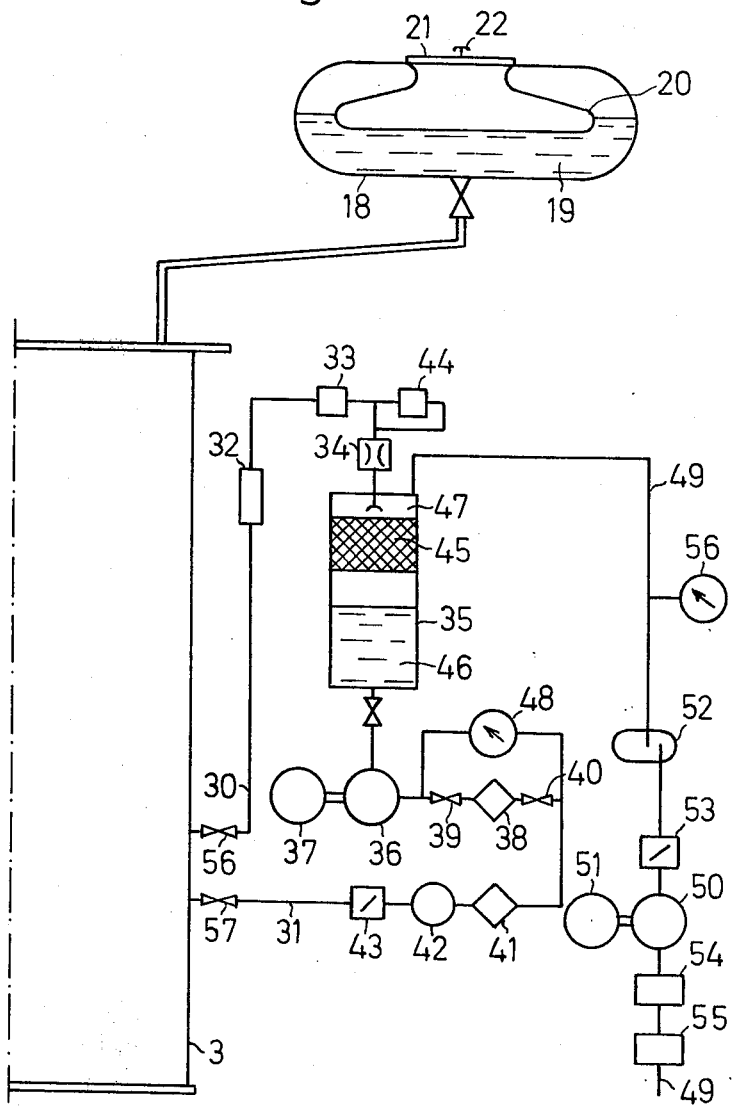
FIG. 3 shows filtering and degassifying equipment diagrammatically, with the understanding that this is to be normally built-on and an integrated part of the transformer construction shown by FIG. 1.

The transformer is also connected to a circuit, as can be seen in FIG. 3. Oil from the transformer is led to the inlet 30 of the circuit and returned to the transformer from its outlet 31. Between its inlet 30 and its outlet 31 the circuit includes a thermostatically regulated electric heating device 32 for in-coming oil, a coarse filter 33 to remove particles coarser than 200 $\mu$, a flow-regulating valve 34 which is controlled by a transducer (not shown) which senses the oil level in the degassing chamber 35 which is also included in the circuit, an oil pump 36 driven by a motor 37, a fine filter 38 for removing particles coarser than 5 $\mu$, surrounded by valves 39 and 40 and which can be closed when changing the filter 38, a gas trap 41 which collects any gas bubbles which may have entered during replacement of the filter 38, a liquid meter 42 of conventional type for measuring the quantity of oil passing through, and a non-return valve 43. A measuring device 44 is located prior to the degassing chamber 35 to measure the moisture content of the oil, this device being connected in a branch or shunt pipe. The measuring device may consist of a paper strip (not shown) arranged in the oil flow, the moisture content of this strip assuming the same value as the paper insulation in the transformer, and which can be determined intermittently, for instance, by extraction of water from the paper strip. The degassing tank 35 contains a filling 45 of Raschig rings or similar filler bodies, to provide a greater surface for the oil streaming down via the outlet end of the pipe 30, from above onto the filler bodies. As mentioned earlier, the oil 46 is kept at the desired level by regulation of the oil supply by means of the valve 34. The space 47 above the filler bodies is connected to a vacuum pump as will be seen in the following. In a branch pipe around the fine filter 38, a differential pressure gauge 48 is arranged to check that the filter does not become clogged.

A vacuum pump 50 is connected by a pipe 49 to the space 47 in the degassing chamber 35 for evacuation thereof. The vacuum pump is driven by a motor 51. The pipe 49 is also provided with an air-cooled, conventional oil condensor 52, a non-return valve 53, a water separator 54 in the form of an air-cooled condensor and a means 55 for determining combustible and incombustible gases liberated during the degassing process. This device is more clearly described later on with reference to FIG. 4. A pressure gauge 56 is also connected to the pipe 49.

At the connection points to the circulation circuit the transformer is provided with open-and-shut valves 56 and 57. The circuit with the degassing chamber and vacuum pump is operation is preferably continuously connected to the transformer so that degassing is performed without interruption. The quantity of oil led from the transformer through the circuit for degassing and back again to the transformer may be up to 10 liters a minute, for instance. The pressure effected by the vacuum pump 50 in the degassing chamber 47 may be up to 0.5 Torr. It is advantageous to perform degassing of the transformer in accordance with the present invention even before it is taken into operation, as when it is used as spare unit, so that the oxygen concentration in the oil is already low when the transformer is started up.

The device 55 mentioned earlier, for determining the gas quantities, is shown in more detail in FIGS. 4a and 4b, the first figure showing the device collecting gas and the second showing the device during analysis. The device comprises a dosing section and an analysis section. The dosing section has two containers 60 and 61. The container 60 is divided to form two spaces 62 and 63, separated from each other by a rolling membrane 64 of, for example, rubber. The space 62 is in communication with the open air by way of the hole 65, whereas the space 63 is only in communication with the pipe 66. Similarly, the container 61 is divided into two spaces 67 and 68 which are separated from each other by a rolling membrane 69 of the same type as membrane 64. The space 67 is in communication with the open air via the hole 70 whereas the space 68 is only in communication with the pipe 71. A body 72 abuts the rolling membrane 64 and a body 73 abuts the rolling membrane 69. These bodies are connected to each other by a rod 74 which keeps the bodies at a constant distance from each other. The rod passes through an aperture 75 in the partition 76 between spaces 63 and 67 in the containers 60 and 61 and through an aperture in membrane 64. The rod is journaled in the aperture 75 with an axial bearing 77, while being sealed to the hole 75 by means of radial lip seals 78 and 79 and to the aperture in the membrane by means of a clamp plate clamping the membrane firmly against the body 72.

The pipes 66 and 71 are joined to a switchable magnetic valve 80. This can be set to have the positions shown in FIGS. 4a and 4b, respectively. In the former case the pipe 66 is in communication with the open air via the valve 80 and the pipe 71 is in communication with the pipe 49 from the degassing chamber via the valve 80. The non-return valve 81 in the pipe 82 is closed at this time. In the latter case the communication from the pipe 66 with the open air is closed, as is the communication between pipe 71 and pipe 49, whereas the non-return valve 81 permits gas to flow from the pipes 66 and 71 to the open air through pipe 82.

As well as the non-return valve 81, the pipe 82 also contains a throttle valve 83 which permits regulation of the flow through the pipe 82, and a device 84 to determine the content of combustible gas in a gas mixture. The device 84 consists of an electric bridge connection 85 with four resistors 86, 87, 88, 89, the latter two being arranged in the gas flow through the pipe 82 and the former two being arranged outside the gas flow. The resistor 89 is surrounded by a porous body 90 containing a catalyst, for instance platinum, for burning combustible gases, whereas the resistor 88 is surrounded by a similar body 91 without catalyst. When a gas mixture containing combustible gases is carried past resistors 88 and 89, the catalytic combustion of the combustible gases caused by the temperature increase occurring, effects a change in the resistance of the resistor 89, thus bringing about an alteration in voltage difference over the volt meter 92. The device 84 can be calibrated with known mixtures of combustible and incombustible gases which are led from the space 68 (when filled) to the device 84 together with air from the space 63 (when filled). Thus, with the help of readings from the volt meter 92 for a certain gas mixture, it is possible to determine the content of combustible gases therein.

The device operates in the following manner: During a period when gas is being collected for analysis, the magnetic valve is set in the position shown in FIG. 4a. The gas from the pipe 49 is then forced by the pump 50 through the pipe 71 into the space 68 and moves the body 73, together with the membrane 69 upwards. Since the body 72 is joined to the body 73, the body 72 is moved up at the same time, together with the membrane 64, whereby air is drawn into the space 63 through the pipe 66 and valve 80. The volume of the space 63 is such that in relation to the volume of the space 68 the quantity of oxygen in the space 63 constitutes an excess in relation to the quantity required for combustion of the combustible gases in the space 68. When the body 73 has been forced up so far that it reaches the top of the container 61 or some other maximum level, and so the body 72 has reached its highest point, the valve 80 is moved to the position shown in FIG. 4b. The change in the position of the valve 80 is effected by a level switch which is actuated by the level of the body 72 or the body 73. If the gas flow is slight, it may take several hours, or even several days before the space 68 and thus the space 63 is filled and before the valve alters position.

When the valve has changed position to that shown in FIG. 4b, the space 68 is emptied of gas through the pipe 71 and the space 63 of air through the pipe 66 and these gases pass together through the pipe 82 and the device 84. The spaces 68 and 63 are emptied making use of the weight of the bodies 72 and 73. These bodies therefore have such a weight that they can be lifted by the gas pressure during the collecting period, but are sufficiently heavy to press out the gases for analysis in the device 84 during the emptying phase. It is not in fact necessary to exploit the weight of the bodies 72 and 73 since the movement can be established making use of spring force (not shown), for instance, in which case the containers need not be located in vertical position. However, it is an advantage to use the weight of the bodies as described since the containers are then emptied at a constant rate and the device is also simple. It normally only takes a few minutes to empty the spaces 63 and 68 and analyze the gas mixture. When the body 73 reaches the bottom of the container 61 or some other lowest point, and so the body 72 has also reached its lowest point, the valve 80 is again switched to the position shown in FIG. 4a, whereupon a new collecting period for gas from the pipe 49 is initiated. Alteration of the position of the valve 80 can be effected by a level switch (not shown) of a type similar to that mentioned previously.

If the volume of the gas collected from the pipe 49 is known (the volume of the space 68 when filled) and by determining the content of combustible and incombustible gases in the gas collected by means of the device 84, and by determining the quantity of oil passing the liquid meters 42 (FIG. 3) during the collecting period for the gas in space 68, the total content of gases in the oil can be determined as well as the content of combustible gases and of incombustible gases. Efficient supervision of the transformer is thus obtained, enabling steps to be taken quickly in the event of disturbances in operation. The determination of the content of combustible and incombustible gases in the oil can be performed automatically with the aid of suitable electronic equipment (not shown).

The present invention is also applicable to other liquid dielectrics than oil, the aging of which is influenced by oxygen in a similar way as that of oil, and to other solid dielectrics than those of cellulose, the aging of which is influenced by oxygen in a similar way as that of cellulose.

What is claimed is:

1. An apparatus for collecting a combustible gas under pressure and determining the amount of combustible constituents therein,
   comprising a first chamber forming a first space having a movable first variable displacement means, a second chamber forming a second space having a movable second variable displacement means, means for interconnecting said displacement means so that by movement thereof they vary the displacements of said chambers with a fixed ratio of displacement therebetween, said displacements means being biased to move in directions reducing the volumes of said spaces, feeding means for feeding said combustible gas to said first space to move the first displacement means against the bias while thereby moving the second displacement means to increase the volume of said second space and for feeding an oxidizing gas to said second space, discharge means for thereafter closing said chambers to said feeding and interconnecting the chambers to a common discharge conduit so that the two displacement means via their bias displace the combustible gas and oxidizing gas together to said conduit.

2. The apparatus of claim 1 having an indicating means responsive to the proportion of combustible constituents of the combustible gas, said conduit being connected to feed this indicating means.

3. The apparatus of claim 2 in which said feeding means for said combustible gas includes means for removing any water in said combustible gas, and said indicating means includes a catalytic element which heats by catalytic reaction between said combustible and oxidizing gases, said element being positioned in the flow from said conduit, and read-out means responsive to the temperature of said element.

4. The apparatus of claim 1 in which said chambers each have a movable end wall for the spaces it forms, thereby forming said variable displacement means, and these walls of the chambers are mechanically interconnected for simultaneous movement together, said feeding means is for increasing the pressure of said combustible gas and connecting said combustible gas with said first chamber's space inside of its movable end wall, and for connecting said second chamber's space inside of its movable end wall with a source of oxidizing gas.

5. The apparatus of claim 4 in which said end walls move vertically and have weight biasing them in said directions.

* * * * *